(12) United States Patent
Mathis et al.

(10) Patent No.: US 7,887,582 B2
(45) Date of Patent: *Feb. 15, 2011

(54) DEVICE AND METHOD FOR MODIFYING THE SHAPE OF A BODY ORGAN

(75) Inventors: Mark L. Mathis, Fremont, CA (US); David Reuter, Bothell, WA (US); Lucas Gordon, Vashon, WA (US); Cruz Beeson, Sacramento, CA (US); Garrett Beget, Bothell, WA (US); Frederick Stewart, Bellevue, WA (US)

(73) Assignee: Cardiac Dimensions, Inc., Kirkland, WA (US)

( * ) Notice: Subject to any disclaimer, the term of this patent is extended or adjusted under 35 U.S.C. 154(b) by 816 days.

This patent is subject to a terminal disclaimer.

(21) Appl. No.: 10/840,188

(22) Filed: May 5, 2004

(65) Prior Publication Data
US 2005/0010240 A1 Jan. 13, 2005

Related U.S. Application Data

(60) Provisional application No. 60/476,693, filed on Jun. 5, 2003.

(51) Int. Cl.
*A61F 2/24* (2006.01)
(52) U.S. Cl. .................... 623/2.37; 128/898
(58) Field of Classification Search ............ 623/1.11, 623/2.36, 2.37, 1.1, 1.12, 1.15, 1.16, 1.18, 623/1.2; 606/108, 198, 191–192, 194–195; 128/898

See application file for complete search history.

(56) References Cited

U.S. PATENT DOCUMENTS 3,974,526 A 8/1976 Dardik et al.
(Continued)

FOREIGN PATENT DOCUMENTS

EP 0893133 1/1999
(Continued)

OTHER PUBLICATIONS

Mathis et al., U.S. Appl. No. 11/782,490 entitled "Device and method for modifying the shape of a body organ," filed Jul. 24, 2007.
(Continued)

*Primary Examiner*—Anhtuan T Nguyen
*Assistant Examiner*—Tuan V Nguyen
(74) *Attorney, Agent, or Firm*—Shay Glenn LLP

(57) ABSTRACT

A tissue shaping device adapted to be deployed in a lumen to modify the shape of target tissue adjacent to the lumen. In one embodiment the device includes first and second anchors; a connector disposed between the first and second anchors; and a focal deflector disposed between the first and second anchors and may be adapted to extend away from the lumen axis and toward the target tissue and/or away from the lumen axis and away from the target tissue when the device is deployed in the lumen. The invention is also a method of modifying target tissue shape. The method includes the steps of providing a tissue shaping device comprising proximal and distal anchors, a connector disposed between the proximal and distal anchors, and a focal deflector; placing the tissue shaping device in a lumen adjacent the target tissue; applying a shaping force from the focal deflector against a lumen wall to modify the shape of the target tissue; and expanding the proximal and distal anchors to anchor the device in the lumen.

6 Claims, 9 Drawing Sheets

U.S. PATENT DOCUMENTS

| | | | |
|---|---|---|---|
| 3,995,623 A | 12/1976 | Blake et al. |
| 4,055,861 A | 11/1977 | Carpentier et al. |
| 4,164,046 A | 8/1979 | Cooley |
| 4,485,816 A | 12/1984 | Krumme |
| 4,550,870 A | 11/1985 | Krumme et al. |
| 4,588,395 A | 5/1986 | Lemelson |
| 4,830,023 A | 5/1989 | de Toledo et al. |
| 5,061,277 A | 10/1991 | Carpentier et al. |
| 5,099,838 A | 3/1992 | Bardy |
| 5,104,404 A | 4/1992 | Wolff |
| 5,250,071 A | 10/1993 | Palermo |
| 5,261,916 A | 11/1993 | Engelson |
| 5,265,601 A | 11/1993 | Mehra |
| 5,350,420 A | 9/1994 | Cosgrove et al. |
| 5,433,727 A | 7/1995 | Sideris |
| 5,441,515 A | 8/1995 | Khosravi et al. |
| 5,449,373 A | 9/1995 | Pinchasik et al. |
| 5,454,365 A | 10/1995 | Bonutti |
| 5,458,615 A | 10/1995 | Klemm et al. |
| 5,474,557 A | 12/1995 | Mai |
| 5,507,295 A | 4/1996 | Skidmore |
| 5,507,802 A | 4/1996 | Imran |
| 5,514,161 A | 5/1996 | Limousin |
| 5,554,177 A | 9/1996 | Kieval et al. |
| 5,562,698 A | 10/1996 | Parker |
| 5,575,818 A | 11/1996 | Pinchuk |
| 5,584,867 A | 12/1996 | Limousin et al. |
| 5,601,600 A | 2/1997 | Ton |
| 5,662,703 A | 9/1997 | Yurek et al. |
| 5,676,671 A | 10/1997 | Inoue |
| 5,733,325 A | 3/1998 | Robinson et al. |
| 5,741,297 A | 4/1998 | Simon |
| 5,752,969 A | 5/1998 | Cunci et al. |
| 5,800,519 A | 9/1998 | Sandock |
| 5,824,071 A | 10/1998 | Nelson et al. |
| 5,836,882 A | 11/1998 | Frazin |
| 5,871,501 A | 2/1999 | Leschinsky et al. |
| 5,891,193 A | 4/1999 | Robinson et al. |
| 5,895,391 A | 4/1999 | Farnholtz |
| 5,899,882 A | 5/1999 | Waksman et al. |
| 5,908,404 A | 6/1999 | Elliott |
| 5,928,258 A | 7/1999 | Khan et al. |
| 5,935,161 A | 8/1999 | Robinson et al. |
| 5,954,761 A | 9/1999 | Machek et al. |
| 5,961,481 A | 10/1999 | Serman et al. |
| 5,961,545 A | 10/1999 | Lentz et al. |
| 5,978,705 A | 11/1999 | KenKnight et al. |
| 5,984,944 A | 11/1999 | Forber |
| 6,007,519 A | 12/1999 | Rosselli |
| 6,015,402 A | 1/2000 | Sahota |
| 6,022,371 A | 2/2000 | Killion |
| 6,027,517 A | 2/2000 | Crocker et al. |
| 6,053,900 A | 4/2000 | Brown et al. |
| 6,056,775 A | 5/2000 | Borghi et al. |
| 6,077,295 A | 6/2000 | Limon et al. |
| 6,077,297 A | 6/2000 | Robinson et al. |
| 6,080,182 A | 6/2000 | Shaw et al. |
| 6,086,611 A | 7/2000 | Duffy et al. |
| 6,096,064 A | 8/2000 | Routh |
| 6,099,549 A | 8/2000 | Bosma et al. |
| 6,099,552 A | 8/2000 | Adams |
| 6,129,755 A | 10/2000 | Mathis et al. |
| 6,171,320 B1 | 1/2001 | Monassevitch |
| 6,183,512 B1 | 2/2001 | Howanec et al. |
| 6,190,406 B1 | 2/2001 | Duerig et al. |
| 6,200,336 B1 | 3/2001 | Pavcnik et al. |
| 6,210,432 B1 | 4/2001 | Solem et al. |
| 6,228,098 B1 | 5/2001 | Kayan et al. |
| 6,241,757 B1 | 6/2001 | An et al. |
| 6,254,628 B1 | 7/2001 | Wallace et al. |
| 6,267,783 B1 | 7/2001 | Letendre et al. |
| 6,275,730 B1 | 8/2001 | KenKnight et al. |
| 6,312,446 B1 | 11/2001 | Huebsch et al. |
| 6,334,864 B1 | 1/2002 | Amplatz et al. |
| 6,342,067 B1 | 1/2002 | Mathis et al. |
| 6,345,198 B1 | 2/2002 | Mouchawar et al. |
| 6,352,553 B1 | 3/2002 | van der Burg et al. |
| 6,352,561 B1 | 3/2002 | Leopold et al. |
| 6,358,195 B1 | 3/2002 | Green et al. |
| 6,395,017 B1 | 5/2002 | Dwyer et al. |
| 6,402,781 B1 | 6/2002 | Langberg et al. |
| 6,419,696 B1 | 7/2002 | Ortiz et al. |
| 6,442,427 B1 | 8/2002 | Boute et al. |
| 6,464,720 B2 | 10/2002 | Boatman et al. |
| 6,503,271 B2 | 1/2003 | Duerig et al. |
| 6,537,314 B2 | 3/2003 | Langberg et al. |
| 6,562,067 B2 | 5/2003 | Mathis |
| 6,569,198 B1 | 5/2003 | Wilson et al. |
| 6,589,208 B2 | 7/2003 | Ewers et al. |
| 6,599,314 B2 | 7/2003 | Mathis et al. |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 6,629,534 B1 | 10/2003 | St. Goar et al. |
| 6,629,994 B2 | 10/2003 | Gomez et al. |
| 6,643,546 B2 | 11/2003 | Mathis et al. |
| 6,648,881 B2 | 11/2003 | KenKnight et al. |
| 6,652,538 B2 | 11/2003 | Kayan et al. |
| 6,656,221 B2 | 12/2003 | Taylor et al. |
| 6,676,702 B2 | 1/2004 | Mathis |
| 6,689,164 B1 | 2/2004 | Seguin |
| 6,709,425 B2 | 3/2004 | Gambale et al. |
| 6,716,158 B2 | 4/2004 | Raman et al. |
| 6,718,985 B2 | 4/2004 | Hlavka et al. |
| 6,721,598 B1 | 4/2004 | Helland et al. |
| 6,723,038 B1 | 4/2004 | Schroeder et al. |
| 6,733,521 B2 | 5/2004 | Chobotov et al. |
| 6,743,219 B1 | 6/2004 | Dwyer et al. |
| 6,764,510 B2 | 7/2004 | Vidlund et al. |
| 6,773,446 B1 | 8/2004 | Dwyer et al. |
| 6,776,784 B2 | 8/2004 | Ginn |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,800,090 B2 | 10/2004 | Alferness et al. |
| 6,805,128 B1 | 10/2004 | Pless et al. |
| 6,810,882 B2 | 11/2004 | Langberg et al. |
| 6,821,297 B2 | 11/2004 | Snyders |
| 6,824,562 B2 | 11/2004 | Mathis et al. |
| 6,827,690 B2 | 12/2004 | Bardy |
| 6,881,220 B2 | 4/2005 | Edwin et al. |
| 6,899,734 B2 | 5/2005 | Castro et al. |
| 6,908,478 B2 * | 6/2005 | Alferness et al. ............ 623/1.11 |
| 6,935,404 B2 | 8/2005 | Duerig et al. |
| 6,964,683 B2 | 11/2005 | Kowalsky et al. |
| 6,966,926 B2 | 11/2005 | Mathis |
| 7,152,605 B2 | 12/2006 | Khairkhahan et al. |
| 7,175,653 B2 | 2/2007 | Gaber |
| 2001/0018611 A1 | 8/2001 | Solem et al. |
| 2001/0041899 A1 | 11/2001 | Foster |
| 2001/0044568 A1 | 11/2001 | Langberg et al. |
| 2001/0049558 A1 | 12/2001 | Liddicoat et al. |
| 2002/0016628 A1 | 2/2002 | Langberg et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0087173 A1 | 7/2002 | Alferness et al. |
| 2002/0095167 A1 | 7/2002 | Liddicoat et al. |
| 2002/0103533 A1 | 8/2002 | Langberg et al. |
| 2002/0138044 A1 | 9/2002 | Streeter et al. |
| 2002/0151961 A1 | 10/2002 | Lashinski et al. |

| | | |
|---|---|---|
| 2002/0156526 A1 | 10/2002 | Hlavka et al. |
| 2002/0161377 A1 | 10/2002 | Rabkin |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2003/0018358 A1 | 1/2003 | Saadat |
| 2003/0040771 A1 | 2/2003 | Hyodoh et al. |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083538 A1 | 5/2003 | Adams et al. |
| 2003/0083613 A1 | 5/2003 | Schaer |
| 2003/0088305 A1 | 5/2003 | Van Schie et al. |
| 2003/0130730 A1 | 7/2003 | Cohn et al. |
| 2003/0135267 A1* | 7/2003 | Solem et al. ............. 623/1.18 |
| 2003/0144697 A1 | 7/2003 | Mathis et al. |
| 2003/0171776 A1 | 9/2003 | Adams et al. |
| 2003/0225454 A1 | 12/2003 | Mathis et al. |
| 2003/0236569 A1 | 12/2003 | Mathis et al. |
| 2004/0010305 A1 | 1/2004 | Alferness et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0102840 A1 | 5/2004 | Solem et al. |
| 2004/0111095 A1 | 6/2004 | Gordon et al. |
| 2004/0127982 A1 | 7/2004 | Machold et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153147 A1 | 8/2004 | Mathis |
| 2004/0158321 A1 | 8/2004 | Reuter et al. |
| 2004/0176840 A1 | 9/2004 | Langberg |
| 2004/0193191 A1 | 9/2004 | Starksen et al. |
| 2004/0193260 A1 | 9/2004 | Alferness et al. |
| 2004/0220654 A1 | 11/2004 | Mathis et al. |
| 2004/0220657 A1 | 11/2004 | Nieminen et al. |
| 2004/0243227 A1 | 12/2004 | Starksen et al. |
| 2004/0249452 A1 | 12/2004 | Adams et al. |
| 2004/0260342 A1 | 12/2004 | Vargas et al. |
| 2005/0004667 A1 | 1/2005 | Swinford et al. |
| 2005/0021121 A1 | 1/2005 | Reuter et al. |
| 2005/0027351 A1 | 2/2005 | Reuter et al. |
| 2005/0027353 A1 | 2/2005 | Alferness et al. |
| 2005/0033419 A1 | 2/2005 | Alferness et al. |
| 2005/0038507 A1 | 2/2005 | Alferness et al. |
| 2005/0060030 A1 | 3/2005 | Lashinski et al. |
| 2005/0065598 A1 | 3/2005 | Mathis et al. |
| 2005/0096666 A1 | 5/2005 | Gordon et al. |
| 2005/0096740 A1 | 5/2005 | Langberg et al. |
| 2005/0107810 A1 | 5/2005 | Morales et al. |
| 2005/0119673 A1 | 6/2005 | Gordon et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0137685 A1 | 6/2005 | Nieminen et al. |
| 2005/0149179 A1 | 7/2005 | Mathis et al. |
| 2005/0149180 A1 | 7/2005 | Mathis et al. |
| 2005/0149182 A1 | 7/2005 | Alferness et al. |
| 2005/0187619 A1 | 8/2005 | Mathis et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0209690 A1 | 9/2005 | Mathis et al. |
| 2005/0216077 A1 | 9/2005 | Mathis et al. |
| 2005/0261704 A1 | 11/2005 | Mathis |
| 2005/0272969 A1 | 12/2005 | Alferness et al. |
| 2006/0020335 A1 | 1/2006 | Kowalsky et al. |
| 2006/0030882 A1 | 2/2006 | Adams et al. |
| 2006/0041305 A1 | 2/2006 | Lauterjung |
| 2006/0116758 A1 | 6/2006 | Swinford et al. |
| 2006/0142854 A1 | 6/2006 | Alferness et al. |
| 2006/0161169 A1 | 7/2006 | Nieminen et al. |
| 2006/0167544 A1 | 7/2006 | Nieminen et al. |
| 2006/0173536 A1 | 8/2006 | Mathis et al. |
| 2006/0191121 A1 | 8/2006 | Gordon et al. |
| 2006/0271174 A1 | 11/2006 | Nieminen et al. |
| 2006/0276891 A1 | 12/2006 | Nieminen et al. |
| 2007/0055293 A1 | 3/2007 | Alferness et al. |
| 2007/0066879 A1 | 3/2007 | Mathis et al. |
| 2008/0140191 A1 | 6/2008 | Mathis et al. |

FOREIGN PATENT DOCUMENTS

| | | |
|---|---|---|
| EP | 0903110 A1 | 3/1999 |
| EP | 0968688 A1 | 1/2000 |
| EP | 1050274 A1 | 11/2000 |
| EP | 1095634 A2 | 5/2001 |
| GB | 0741604 | 12/1955 |
| JP | 2754067 | 3/1998 |
| JP | 2000-308652 | 11/2000 |
| JP | 2001-503291 | 3/2001 |
| JP | 2003-503101 | 1/2003 |
| JP | 2003-521310 | 7/2003 |
| WO | WO 98/56435 A1 | 12/1998 |
| WO | WO 00/44313 A1 | 8/2000 |
| WO | WO 00/60995 A3 | 10/2000 |
| WO | WO 00/74603 A1 | 12/2000 |
| WO | WO 01/00111 A1 | 1/2001 |
| WO | WO 01/19292 A1 | 3/2001 |
| WO | WO 01/50985 A1 | 7/2001 |
| WO | WO 01/54618 A1 | 8/2001 |
| WO | WO 01/87180 A2 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/19951 A1 | 3/2002 |
| WO | WO 02/34118 A2 | 5/2002 |
| WO | WO 02/47539 A2 | 6/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 03/015611 A2 | 2/2003 |
| WO | WO 03/037171 A2 | 5/2003 |
| WO | WO 03/049647 A1 | 6/2003 |
| WO | WO 03049648 A2 | 6/2003 |
| WO | WO 03/055417 A1 | 7/2003 |
| WO | WO 03/059198 A2 | 7/2003 |
| WO | WO 03/063735 A2 | 8/2003 |
| WO | WO 2004/045463 A2 | 6/2004 |
| WO | WO 2004/084746 | 10/2004 |

OTHER PUBLICATIONS

Mathis et al., U.S. Appl. No. 11/782,508, entitled "Device and method for modifying the shape of a body organ," filed Jul. 24, 2007.
Mathis et al., U.S. Appl. No. 11/782,527 entitled "Device and method for modifying the shape of a body organ," filed Jul. 24, 2007.
Mathis, et al; U.S. Appl. No. 11/279,352, entitled "Mitral Valve Annuloplasty Device with Vena Cava Anchor," filed Apr. 11, 2006.
Mathis, Mark; U.S. Appl. No. 11/655,710, entitled "Mitral Valve Device Using Conditioned Shape Memory Alloy," filed Jan. 18, 2007.
Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

Heartsite.com. Echocardiogram, 1999; p. 1-4. A.S.M. Systems Inc. Available at: http://www.heartsite.com/html/echocardiogram.html. Accessed Jul. 1, 2005.

Papageorgiou, P., et al., "Coronary Sinus Pacing Prevents Induction of Atrial Fibrillation," Circulation 96: 1893-1898, Sep. 16, 1977.

Reuter et al.; U.S. Appl. No. 12/642,525 entitled "Adjustable Height Focal Tissue Deflector," filed Dec. 18, 2009.

Alferness et al.; U.S. Appl. No. 12/719,758 entitled "Device and Method for Modifying the Shape of a Body Organ," filed Mar. 8, 2010.

Pijls et al.; Measurement of fractional flow reserve to assess the functional severity of coronary-artery stenoses; The New England J. of Med.; vol. 334, No. 26; pp. 1703-1708; Jun. 27, 1996.

Yamanouchi, et al.; Activation Mapping from the coronary sinus may be limited by anatomic variations; vol. 21 pp. 2522-2526; Nov. 1998.

Mathis et al; U.S. Appl. No. 11/963,417 entitled "Device and method for modifying the shape of a body organ," filed Dec. 21, 2007.

El-Maasarany et al.; The coronary sinus conduit function: Anatomical study (relationship to adjacent structures); http://europace.oxfordjournals.org/cge/content/full/7/5/475. (accessed Sep. 9, 2008).

Gordon et al.; U.S. Appl. No. 11/971,174 entitled "Medical device delivery system," filed Jan. 8, 2008.

Nieminen et al; U.S. Appl. No. 12/060,781 entitled "Tissue shaping device," filed Apr. 1, 2008.

Hayner et al.; U.S. Appl. No. 12/189,527 entitled "Catheter cutting tool," filed Aug. 11, 2008.

Pai, Suresh; U.S. Appl. No. 60/329,694 entitled "Percutaneous cardiac support structures and deployment means," filed Oct. 16, 2001.

\* cited by examiner

DEVICE AND METHOD FOR MODIFYING THE SHAPE OF A BODY ORGAN

CROSS-REFERENCE

This application claims the benefit of U.S. Provisional Application No. 60/476,693, filed Jun. 5, 2003, which application is incorporated herein by reference.

BACKGROUND OF THE INVENTION

The mitral valve is a portion of the heart that is located between the chambers of the left atrium and the left ventricle. When the left ventricle contracts to pump blood throughout the body, the mitral valve closes to prevent the blood from being pumped back into the left atrium. In some patients, whether due to genetic malformation, disease or injury, the mitral valve fails to close properly causing a condition known as regurgitation, whereby blood is pumped into the atrium upon each contraction of the heart muscle. Regurgitation is a serious, often rapidly deteriorating, condition that reduces circulatory efficiency and must be corrected.

Two of the more common techniques for restoring the function of a damaged mitral valve are to surgically repair the valve, replace the valve with a mechanical valve, or to suture a flexible ring around the valve to support it. Each of these procedures is highly invasive because access to the heart is obtained through an opening in the patient's chest. Patients with mitral valve regurgitation are often relatively frail thereby increasing the risks associated with such an operation.

One less invasive approach for aiding the closure of the mitral valve involves the placement of a support structure in the cardiac sinus and vessel that passes adjacent the mitral valve. The support structure is designed to push the vessel and surrounding tissue against the valve to aid its closure. This technique has the advantage over other methods of mitral valve repair because it can be performed percutaneously without opening the chest wall. Examples of such devices are shown in U.S. patent application Ser. No. 10/003,910, "Focused Compression Mitral Valve Device and Method;" U.S. patent application Ser. No. 10/142,637, "Body Lumen Device Anchor, Device and Assembly;" U.S. patent application Ser. No. 10/331,143, "System and Method to Effect the Mitral Valve Annulus of a Heart;" and U.S. patent application Ser. No. 10/429,172, "Device and Method for Modifying the Shape of a Body Organ," filed May 2, 2003. The disclosures of these patent applications are incorporated herein by reference.

The purpose of a support device in a lumen such as a vein or artery is to reshape a particular tissue area adjacent to the lumen. In order to be minimally invasive, the reshaping should be limited to the target tissue, such as the mitral valve annulus, and any reshaping of other tissue adjacent to the lumen should be minimized or avoided. For example, to treat mitral valve regurgitation, the device is placed in the coronary sinus to reshape the mitral valve annulus. Care should be taken to minimize the reshaping of other adjacent tissue, such as nearby arteries. See, e.g., the following applications (the disclosures of which are incorporated herein by reference): U.S. patent application Ser. No. 09/855,945, "Mitral Valve Therapy Device, System and Method" (published Nov. 14, 2002, as U.S. 2002/0169504 A1); U.S. patent application Ser. No. 09/855,946, "Mitral Valve Therapy Assembly and Method" (published Nov. 14, 2002, as U.S. 2002/0169502 A1). It is also advisable to monitor cardiac perfusion during and after such mitral valve regurgitation therapy. See, e.g., U.S. patent application Ser. No. 10/366,585, "Method of Implanting a Mitral Valve Therapy Device," the disclosure of which is incorporated herein by reference.

SUMMARY OF THE INVENTION

One aspect of the invention is a tissue shaping device adapted to be deployed in a lumen to modify the shape of target tissue adjacent to the lumen. In one embodiment the device includes first and second anchors; a connector disposed between the first and second anchors; and a focal deflector disposed between the first and second anchors and may be adapted to extend away from the lumen axis and toward the target tissue and/or away from the lumen axis and away from the target tissue when the device is deployed in the lumen. The focal deflector may have an expandable portion that is, e.g., self-expanding or expandable through the application of an actuation force. The device may also have a lock to lock the focal deflector in an expanded configuration.

In some embodiments the focal deflector is integral with the connector. For example, the focal deflector may be a bend in the connector, such as a bend that extends away from the lumen axis and toward the target tissue. The focal deflector may include a local change to the linear shape of the connector, such as a portion of increased curve of the curved line of the connector. The focal deflector may also include a flattened portion of the connector.

In some embodiments the focal deflector includes an expandable anchor and possibly a portion integral with the connector and adapted to extend away from the lumen axis and toward the target tissue when the device is deployed in the lumen.

Another aspect of the invention is a method of modifying target tissue shape. The method includes the steps of providing a tissue shaping device comprising proximal and distal anchors, a connector disposed between the proximal and distal anchors, and a focal deflector; placing the tissue shaping device in a lumen adjacent the target tissue; applying a shaping force from the focal deflector against a lumen wall to modify the shape of the target tissue; and expanding the proximal and distal anchors to anchor the device in the lumen. In some embodiments the expanding step includes the steps of expanding the distal anchor to anchor within the lumen; applying a proximally directed force on the device; and expanding the proximal anchor while applying the proximally directed force.

In some embodiments, the placing step includes the step of orienting the focal deflector away from the lumen axis and toward the target tissue. In other embodiments, the placing step includes the step of orienting the focal deflector away from the lumen axis and away from the target tissue.

The applying step may include the step of expanding the focal deflector, such as by applying an actuation force to the focal deflector. The focal deflector may also be locked in its expanded configuration. In some embodiments the applying and expanding steps may include expanding the distal anchor to anchor within the lumen; applying a proximally directed force on the device; expanding the focal deflector while applying the proximally directed force; applying a proximally directed force on the device after expanding the focal deflector; and expanding the proximal anchor while applying the proximally directed force of the previous step.

Yet another aspect of the invention is a tissue shaping device adapted to be deployed in a lumen to modify the shape of target tissue adjacent to the lumen. In some embodiments the device includes an expandable anchor; a focal deflector; a connector disposed between the anchor and the focal deflector; and a tail extending from the focal deflector away from the anchor. The focal deflector may include an expandable portion. In some embodiments, the focal deflector is adapted to extend away from the lumen axis and away from the target tissue when the device is deployed in the lumen.

One application for the device of this invention is in the treatment of mitral valve regurgitation. The invention will be described in further detail below with reference to the drawings.

DETAILED DESCRIPTION OF THE INVENTION

Tissue shaping devices that apply force to a localized, discrete portion of the vessel wall surrounding a lumen have been described. See, e.g., U.S. patent application Ser. No. 10/003,910, "Focused Compression Mitral Valve Device and Method," which describes the use of such devices disposed in the coronary sinus to treat mitral valve regurgitation. Other therapies deploy one or more rigid devices in the lumen to change the shape of the lumen and adjacent tissue. See, e.g., Lashinski et al. U.S. patent application Ser. No. 10/066,302 (published as U.S. 2002/0151961 A1); Taylor et al. U.S. patent application Ser. No. 10/068,264 (published as U.S. 2002/0183835 A1); Liddicoat et al. U.S. patent application Ser. No. 10/112,354 (published as U.S. 2002/0183838 A1); the disclosures of which are incorporated herein by reference. Still other tissue shaping devices utilize an "anchor and cinch" method to modify tissue adjacent a lumen, i.e., by anchoring a distal anchor, placing a proximally-directed force on a connector extending proximally from the distal anchor, and anchoring a proximal anchor before ceasing the proximally directed force to maintain the device's configuration and the reshaping of the tissue.

The present invention provides a device disposed in a lumen to reshape tissue adjacent to the lumen that includes a focal deflector tissue reshaper, two anchors and an optional connector to help maintain the position of the focal tissue reshaper within the lumen. The use of a focal deflector tissue reshaper aimed at target tissue adjacent to the lumen minimizes the risk of adverse consequences from altering the shape of non-target tissue adjacent to other parts of the lumen. The anchors and/or connector may also be used to help reshape the target tissue.

Figure 1:
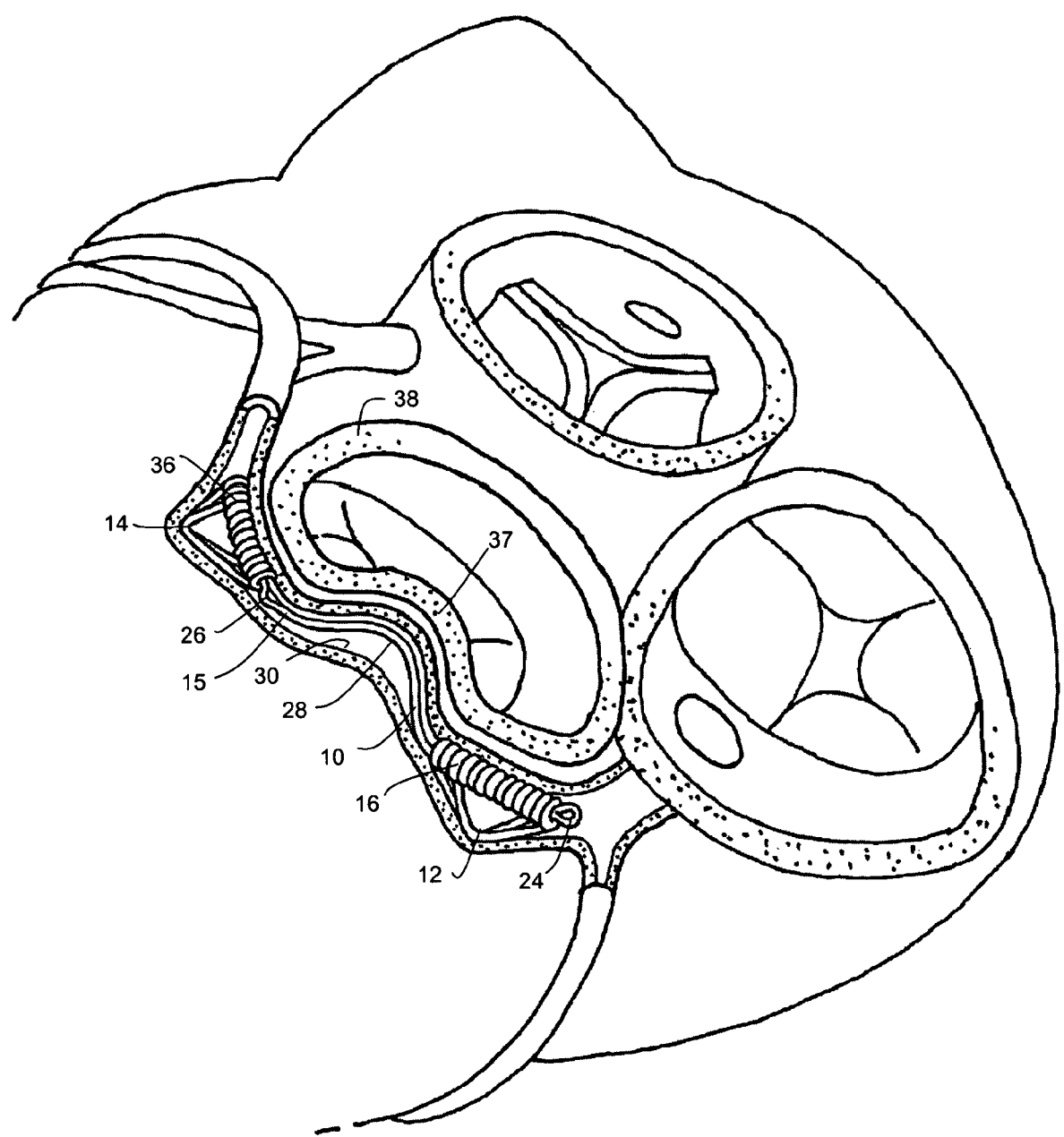
FIG. 1 shows a tissue reshaping device according to one aspect of the invention deployed in a coronary sinus to reshape the mitral valve annulus to treat mitral valve regurgitation.
Figure 2:
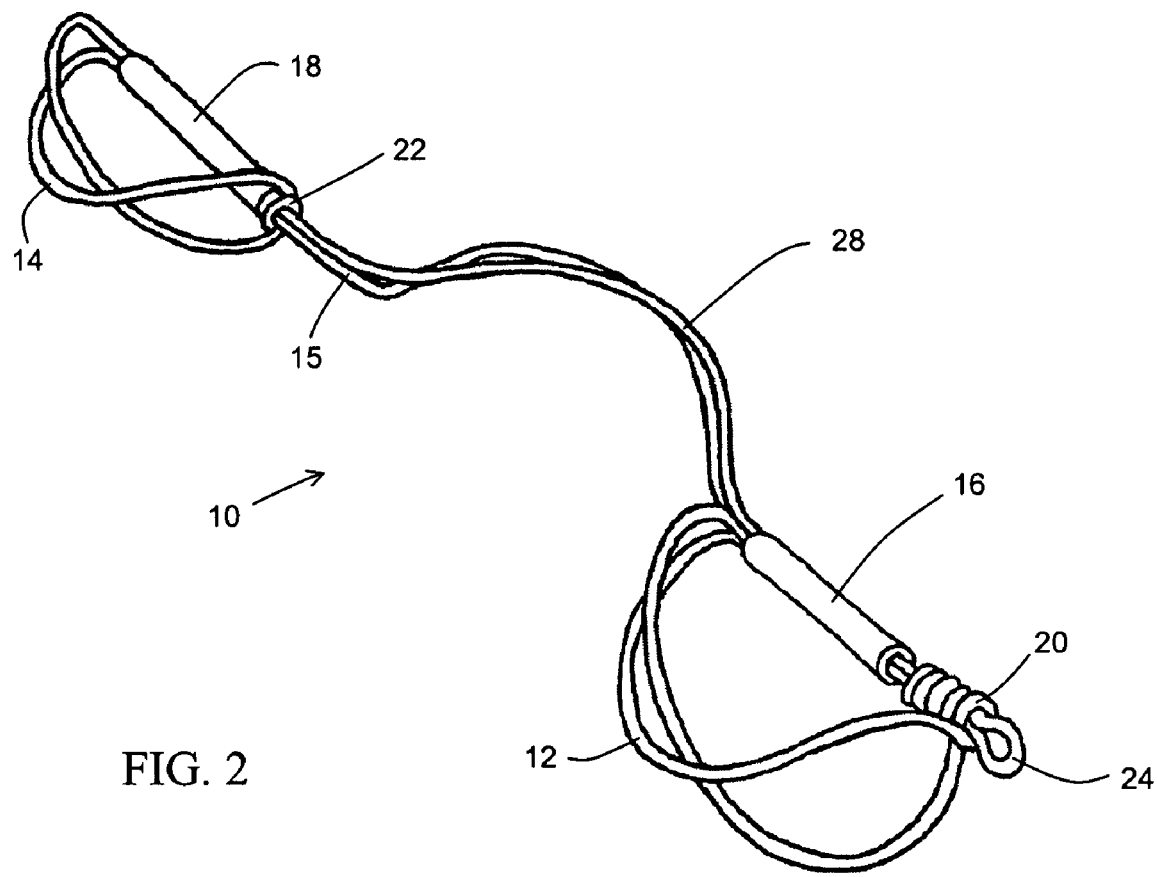
FIG. 2 is a perspective view of the device shown in FIG. 1.

FIGS. 1 and 2 show a tissue reshaping device 10 according to one aspect of this invention. Device 10 is designed to be disposed in the coronary sinus or other cardiac vein to treat mitral valve regurgitation. It should be understood that such devices may also be used in other body lumens to reshape other tissue.

As shown in FIGS. 1 and 2, device 10 has a proximal anchor 12 and a distal anchor 14 connected by a connector 15. In the embodiment shown in FIGS. 1 and 2, the anchors 12 and 14 are formed from metal wire, preferably made from a shape memory material such as nitinol, bent into a figure 8 configuration. Crimps 16 and 18 hold the wire in place and attach the anchors to connector 15. In the embodiment shown in FIG. 1, crimps 16 and 18 are formed from wound wire, such as nitinol. In the embodiment shown in FIG. 2, crimps 16 and 18 are formed from metal tubes, such as titanium tubes.

Device 10 is delivered via a catheter to the treatment site within the lumen in a collapsed or unexpanded configuration. After expelling device 10 from the catheter at the treatment site (either by advancing the device distally out of the end of the catheter or by moving the end of the catheter proximally while maintaining the device stationary), the device's anchors begin to self-expand. At the proximal end of each anchor is an eyelet 20 and 22. Advancing eyelets 20 and 22 distally over corresponding lock bumps 24 and 26 further expands and locks the anchors 12 and 14 in an expanded configuration. Further details of the construction, delivery and deployment of such anchors may be found in U.S. patent application Ser. No. 10/142,637, "Body Lumen Device Anchor, Device and Assembly;" U.S. patent application Ser. No. 10/331,143, "System and Method to Effect the Mitral Valve Annulus of a Heart;" and U.S. patent application Ser. No. 10/429,172, "Device and Method for Modifying the Shape of a Body Organ," filed May 2, 2003. It should be understood that other anchor designs could be used without departing from the invention.

Device 10 has a focal deflector 28 facing away from the anchors 12 and 14 and toward the mitral valve annulus. In this embodiment, focal deflector 28 is formed as a bend in the connector 15. As shown in FIG. 1, when disposed in lumen 30 (shown here as the coronary sinus), the orientation of device 10 places focal deflector 28 against the target tissue 37 to reshape the mitral valve annulus 38. Device 10 may be curved to help ensure this orientation. For delivery via a catheter, focal deflector 28 is deformed and assumes the shape shown in FIGS. 1 and 2 after deployment from the catheter.

Because of the action of focal deflector 28, the desired reshaping of the mitral valve annulus may be achieved with less cinching than other device designs or even with no cinching. Thus, the anchors do not need to anchor as tightly and may be expanded less, thereby minimizing the reshaping of non-target tissue adjacent the anchors. In addition, with less or no cinching, any undesirable effect on non-target tissue adjacent the connector is also minimized. On the other hand, should reshaping adjacent to the anchors and/or connector be desired, such reshaping can be achieved through a combination of expansion of the anchors and cinching of the connector between them. The cinching is performed as with prior devices: by anchoring a distal anchor, placing a proximally-directed force on a connector extending proximally from the distal anchor, and anchoring a proximal anchor before ceasing the proximally directed force to maintain the device's configuration and the reshaping of the tissue.

Figure 3:
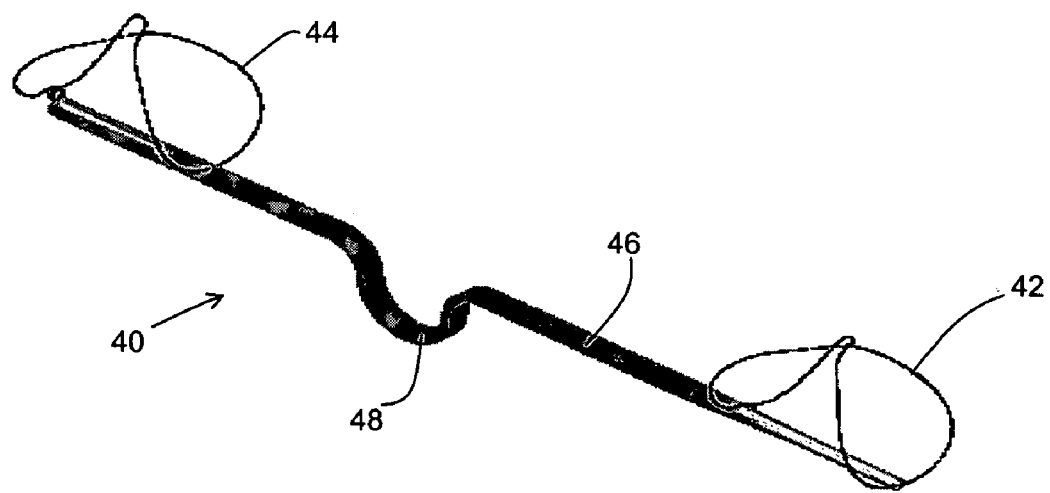
FIG. 3 shows another embodiment of the invention.

FIG. 3 shows another embodiment of the invention. As in the embodiment of FIGS. 1 and 2, device 40 in FIG. 3 has two anchors 42 and 44 connected by a connector 46. Connector 46 is formed as a ribbon, preferably from a shape memory material such as nitinol, with a focal deflector 48 formed therein. The anchors 42 and 44 may be formed like the anchors of the previous embodiment.

In use, device 40 is delivered via catheter to the treatment site in a collapsed or unexpanded configuration. Device 40 is then deployed by expelling it from the catheter and expanding it within a lumen in a position and orientation that places focal deflector 48 against the lumen's vessel wall adjacent to the target tissue to modify the shape of the target tissue. While the device may also be cinched to provide additional reshaping, the amount of cinching required will be less, thereby minimizing the reshaping of any non-target tissue adjacent the lumen by the connector. In addition, as with the previous embodiment, anchors 42 and 44 do not need to be expanded as much, thereby minimizing the reshaping of the non-target tissue adjacent to the anchors.

Figure 4:
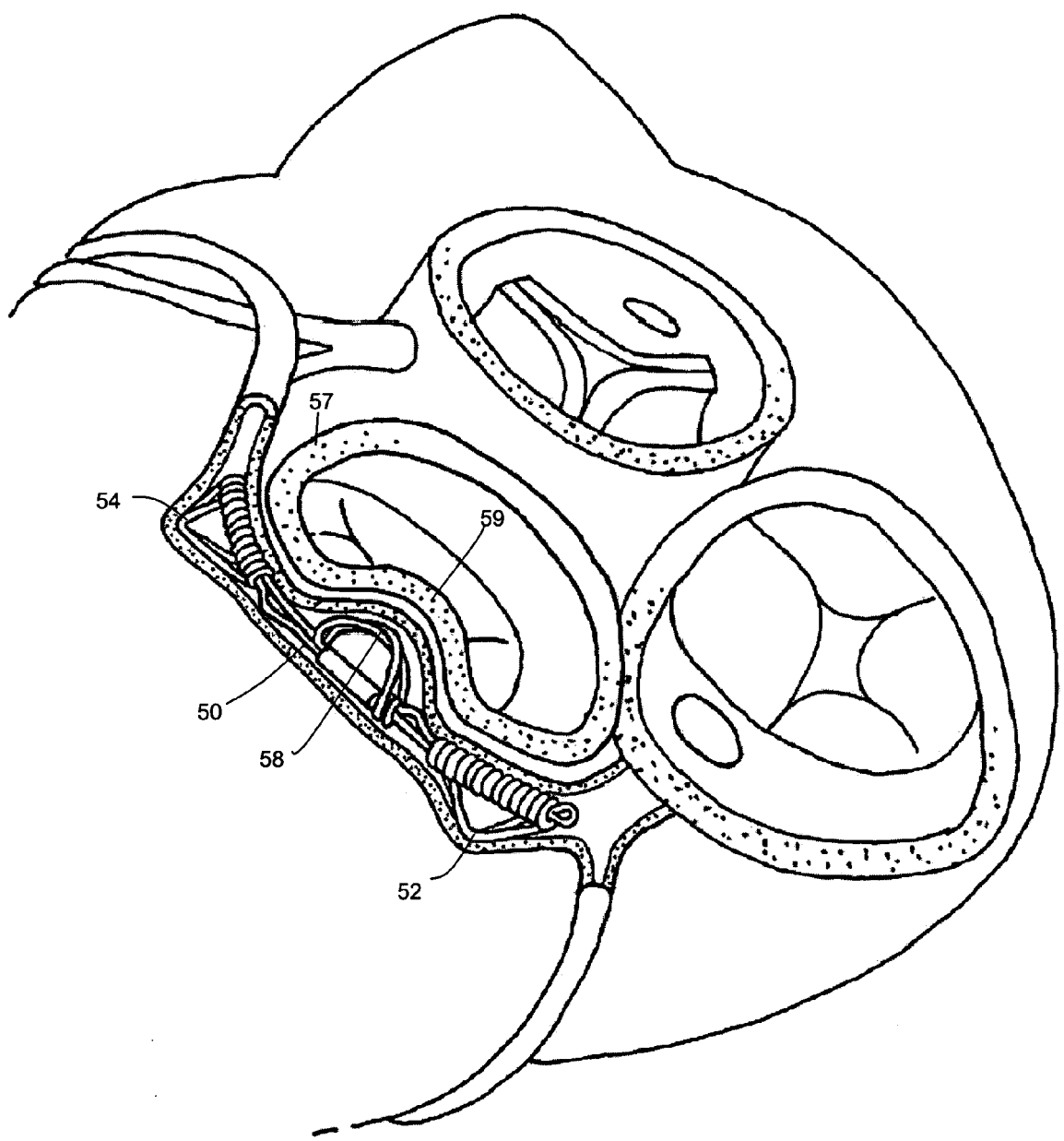
FIG. 4 shows another embodiment of the invention and its use to treat mitral valve regurgitation.
Figure 5:
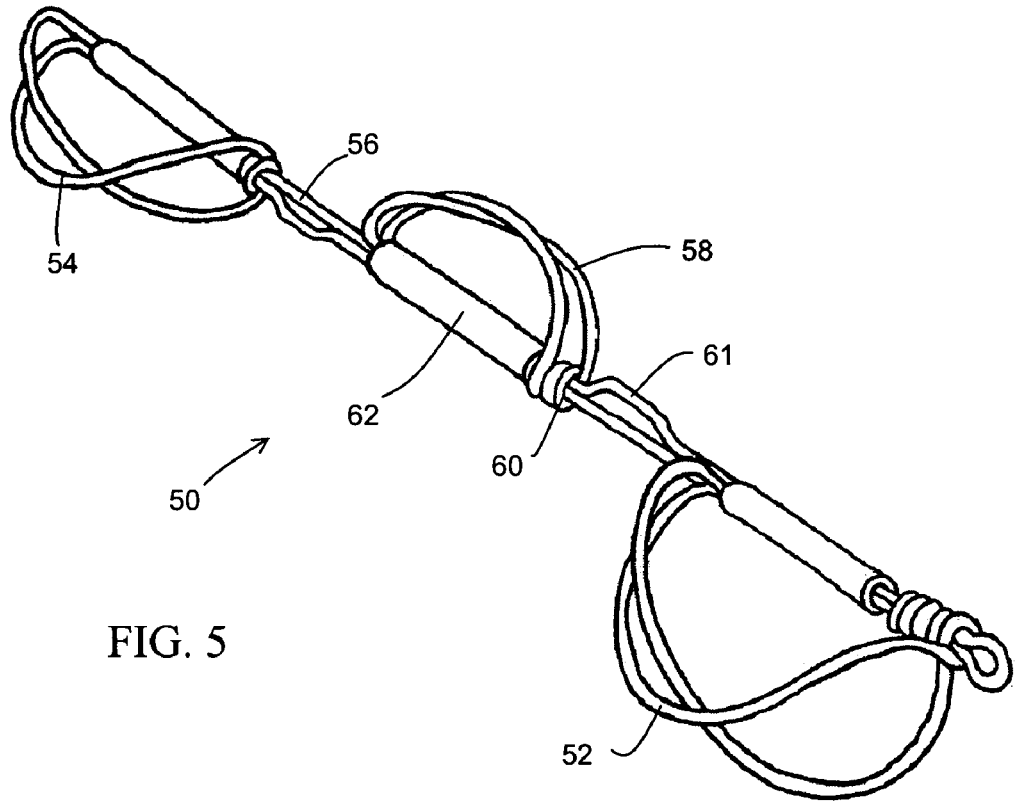
FIG. 5 is a perspective view of the device shown in FIG. 4.

FIGS. 4 and 5 show yet another embodiment of the invention and its use to treat mitral valve regurgitation. Device 50 has proximal and distal anchors 52 and 54 connected by a connector 56. Anchors 52 and 54 are preferably formed like the anchors of the embodiments of FIGS. 1-3.

A focal deflector 58 is disposed on connector 56. In this embodiment, focal deflector 58 has substantially the same design as anchors 52 and 54. Focal deflector 58 is formed from wire (preferably made from a shape memory material such as nitinol) and has a figure 8 configuration when expanded. A crimp 62 attaches the wire to the connector 56. The anchors and focal deflector are delivered via a catheter to the appropriate site within the lumen in an unexpanded configuration, then expanded to a deployed configuration through the application of actuation forces delivered by catheters or other known tools. Like the anchors, focal deflector 58 may be locked in its expanded configuration by advancing an eyelet 60 over a lock bump 61.

As shown in FIG. 4, when disposed in a lumen such as the coronary sinus, the orientation of device 50 places focal deflector 58 against the coronary sinus wall adjacent the target tissue 59 of the mitral valve annulus 57 to reshape the mitral valve annulus. Device 50 may be curved to help ensure proper orientation. As with the other embodiments, because of the action of focal deflector 58, the desired reshaping of the mitral valve annulus may be achieved with less or even with no cinching. Thus, the anchors do not need to anchor as tightly and may be expanded less, thereby minimizing the reshaping of non-target tissue adjacent the anchors. In addition, with less or no cinching, the effect on non-target tissue adjacent the connector is also minimized.

Because it can be expanded and locked like an anchor, the focal deflector 58 of FIGS. 4 and 5 can also be used like an anchor during a cinching operation. For example, after expanding and locking distal anchor 54, a proximally-directed force can be exerted on the portion of connector 56 extending between distal anchor 54 and focal deflector 58 prior to expanding and locking focal deflector 58 to cinch the distal portion of device 50. Likewise, after expanding and locking focal deflector 58, another proximally-directed force can be exerted on the portion of connector 56 extending between focal deflector 58 and proximal anchor 52 prior to expanding and locking proximal anchor 52 to cinch the proximal portion of device 50. If cinching is needed to achieve the desired shape modification of the target tissue, the presence of focal deflector 58 enables a user to cinch the distal and proximal portions of device 50 with different cinching forces.

Figure 6:
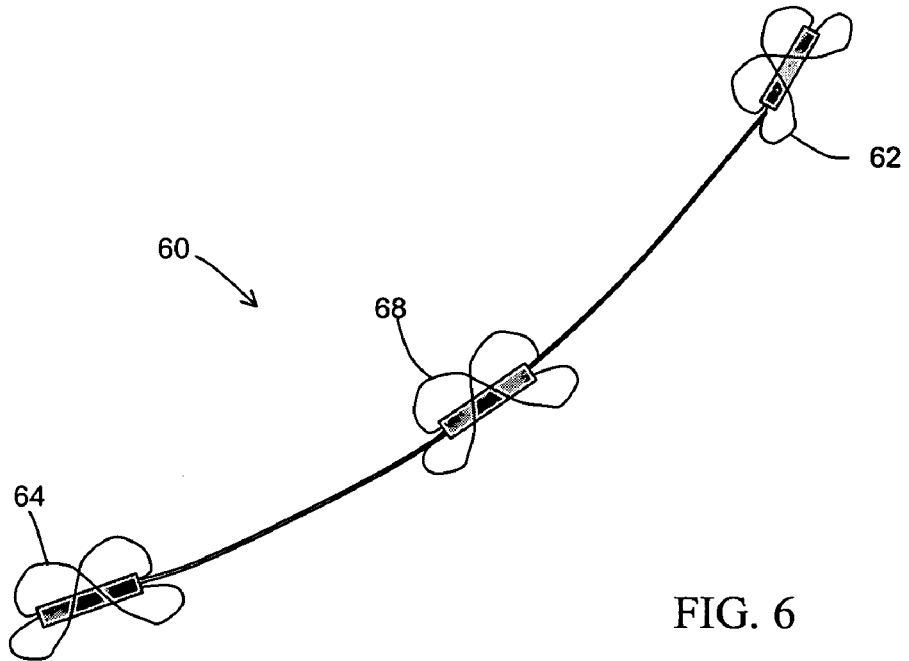
FIG. 6 shows an embodiment in which the focal deflector faces in the same direction as the anchors.

The focal deflector shown in the embodiment of FIGS. 4 and 5 may have other orientations. For example, FIG. 6 shows an embodiment in which the focal deflector 68 of device 60 faces in the same direction as the anchors 62 and 64. In addition, the focal deflector of the embodiments of FIGS. 4-6 may be self-expanding but not locking.

Figure 7:
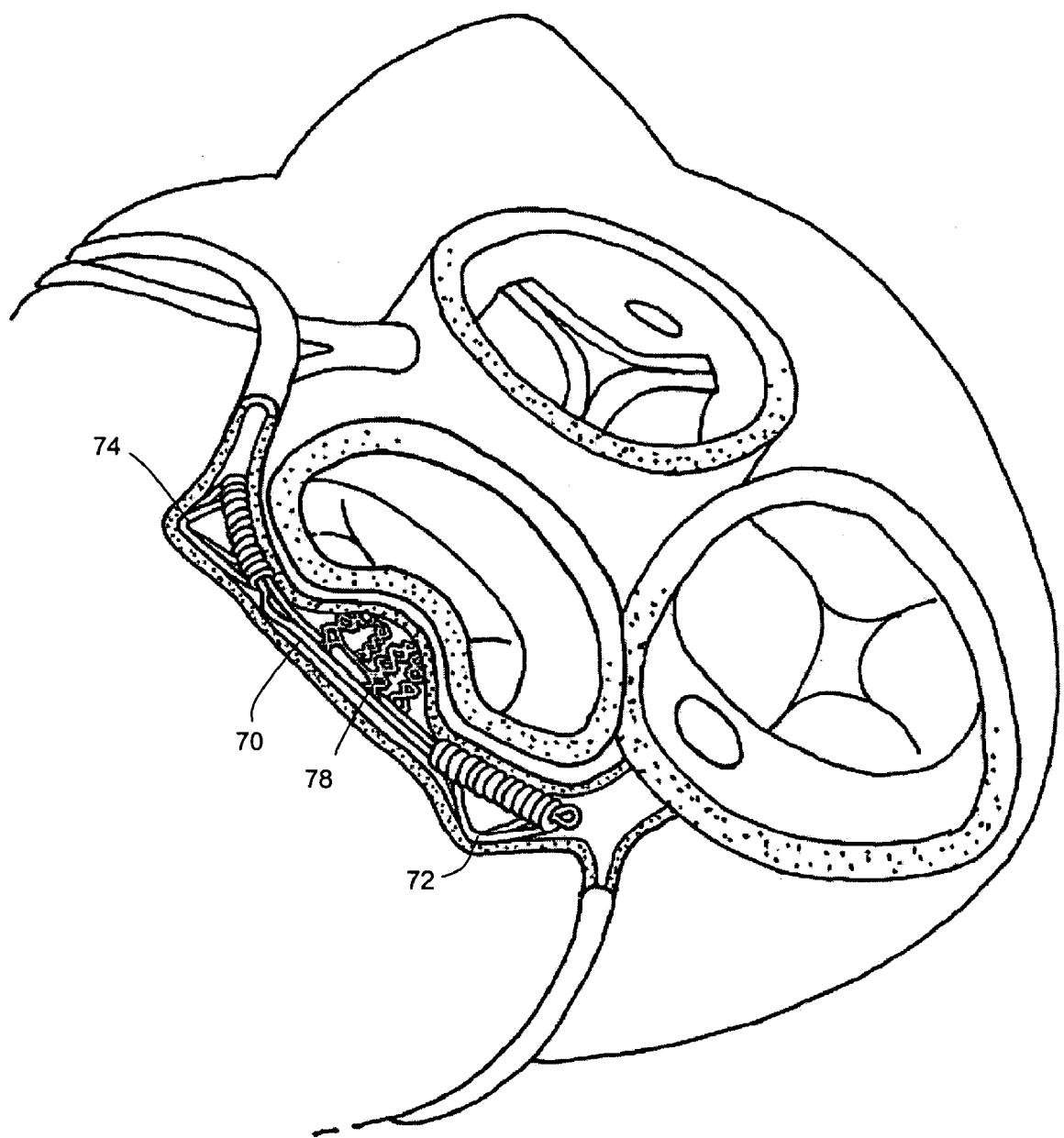
FIG. 7 shows yet another embodiment of the invention deployed in a coronary sinus to reshape the mitral valve annulus to treat mitral valve regurgitation.
Figure 8:
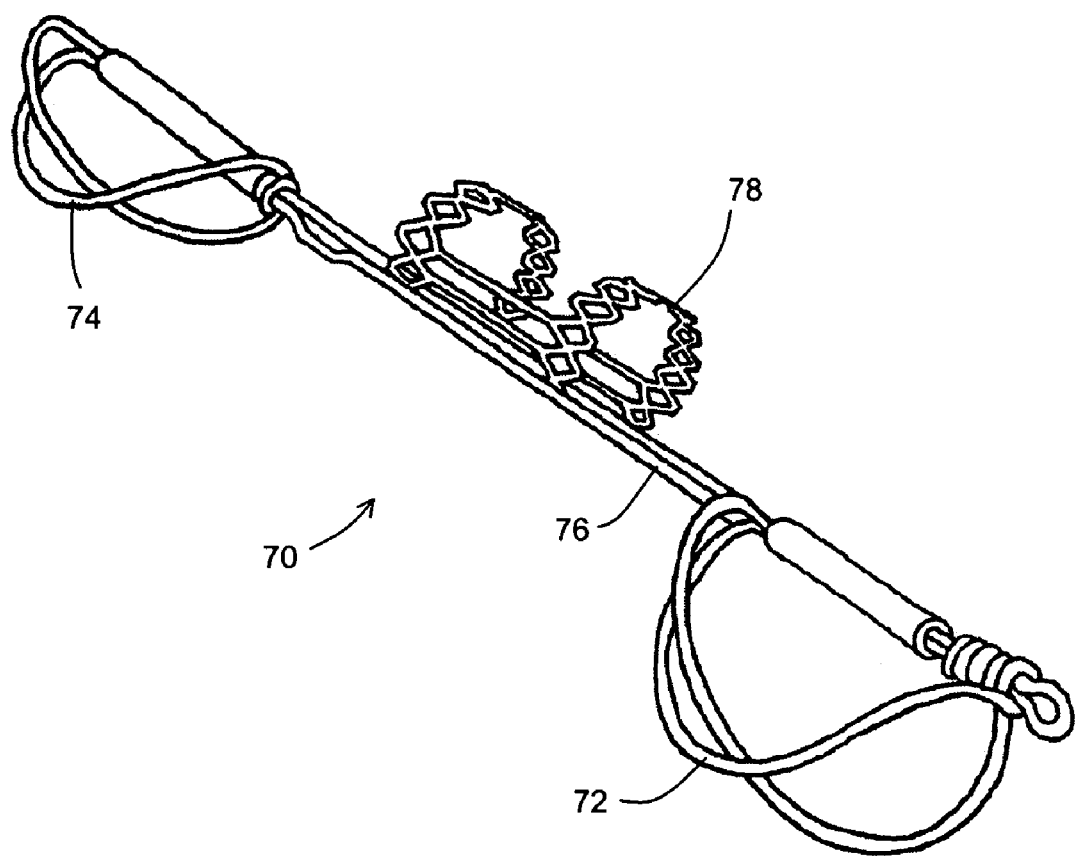
FIG. 8 is a perspective view of the device shown in FIG. 7.

FIGS. 7 and 8 show yet another embodiment of the invention. Like the other embodiments, device 70 has a proximal anchor 72 and a distal anchor 74 connected by a connector 76. Disposed on connector 76 is a focal deflector 78 formed as an expanded cut-out tube, such as a modified stent.

As shown in FIG. 7, device 70 may be deployed in the coronary sinus to treat mitral valve regurgitation by reshaping the tissue adjacent to focal deflector 78. Device 70 is delivered to in an expanded configuration to the treatment site, then expelled from the catheter. Anchors 72 and 74 self-expand, then are further expanded and locked as in the other embodiments. Focal deflector 78 may also self-expand to the configuration shown in FIGS. 7 and 8. Alternatively, focal deflector 78 may be expanded by using a balloon catheter to provide the actuation force, as is well-known in the stent art.

As in the other embodiments, because of the action of focal deflector 78, the desired reshaping of the mitral valve annulus may be achieved with less or even with no cinching. Thus, the anchors do not need to anchor as tightly and may be expanded less, thereby minimizing the reshaping of non-target tissue adjacent the anchors. In addition, with less or no cinching, the effect on non-target tissue adjacent the connector is also minimized.

Figure 9:
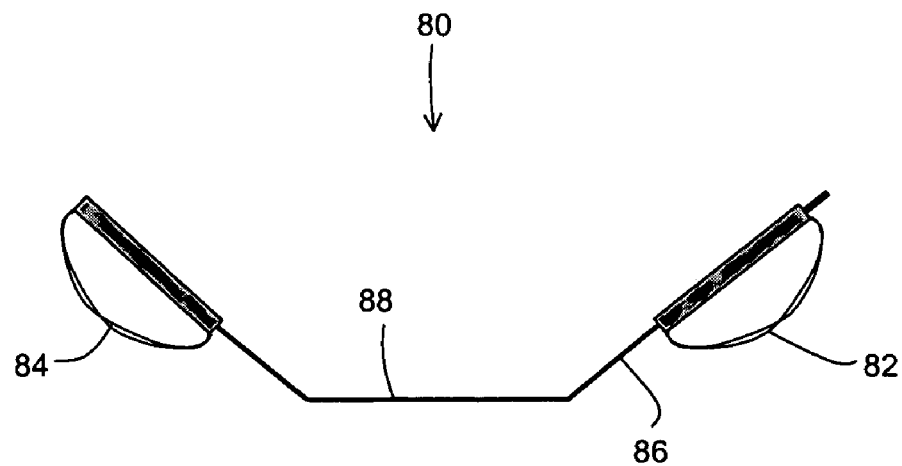
FIG. 9 shows yet another embodiment of the invention.

FIG. 9 shows an embodiment of a device 80 with proximal and distal anchors 82 and 84 with a figure 8 design like other embodiments connected by a connector 86. A focal deflector 88 is formed as a flattened area in connector 86. In this embodiment, connector 86 and focal deflector 88 are formed from shape memory material wire, such as nitinol. While FIG. 9 shows connector 86 and focal deflector 88 as three discrete straight segments, any or all of these elements may be have a curve. In any variation on the embodiment of FIG. 9, however, the focal deflector 88 is straighter than the connector portions extending distally and proximally from it to the distal and proximal anchors, respectively. Device 80 may be delivered and deployed at the treatment site in the same manner as the embodiments described above.

Figure 10:
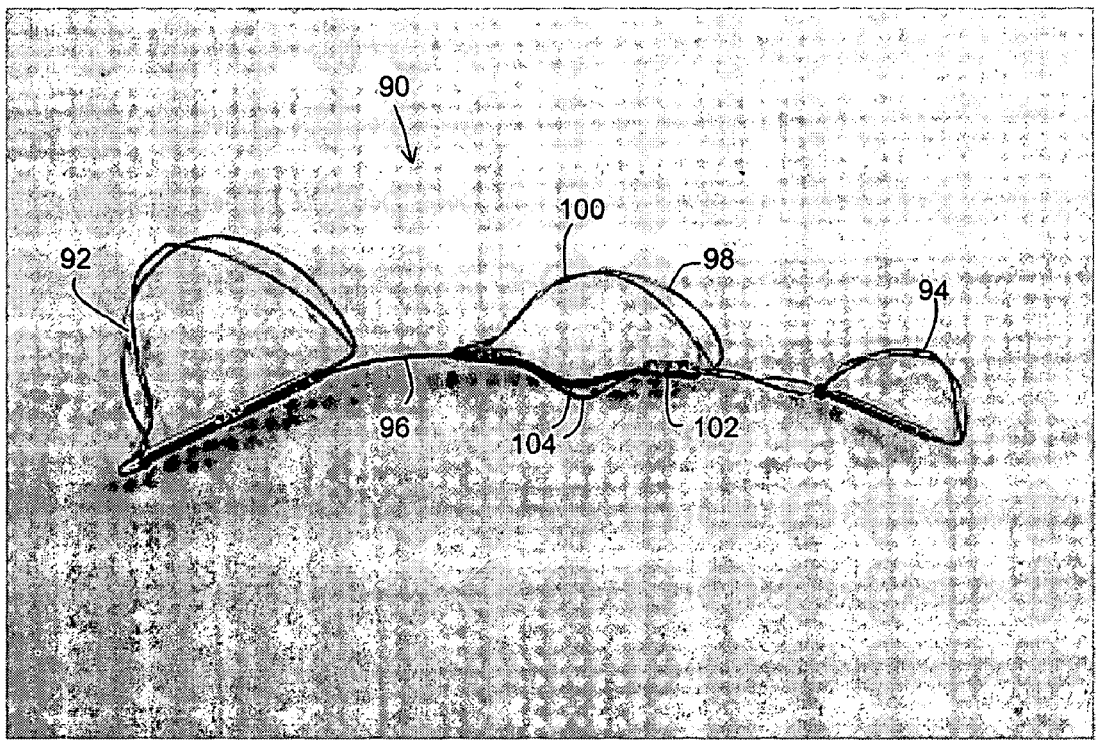
FIG. 10 shows still another embodiment of the invention.
Figure 11:
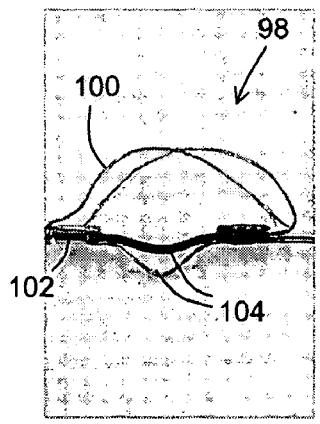
FIG. 11 shows the focal deflector of the embodiment of FIG. 10.
Figure 12:
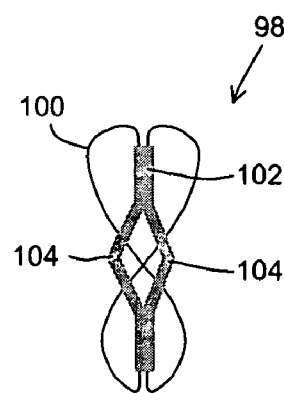
FIG. 12 is yet another view of the focal deflector of the embodiment of FIG. 10.

FIGS. 10-12 show yet another embodiment of a device 90 with proximal and distal anchors 92 and 94 with a figure 8 design like other embodiments connected by a connector 96. A focal deflector 98 is also formed with a wire 100 (preferably made from a shape memory material such as nitinol) bent into a figure 8 pattern. As shown in more detail in FIGS. 11 and 12, instead of a wrapped wire or solid metal crimp, focal deflector 98 has a base 102 with two downwardly extending struts 104. The angular spread between struts 104 helps orient the device within the lumen. Base 102 may be made from a laser-cut shape memory material such as nitinol. The combination of the expansion of anchor wire 100 (as in the embodiment shown in FIG. 6) with the downward pressure from struts 104 (as in the embodiments shown in FIGS. 1-3) provide for focal deflection of target tissue adjacent to the focal deflector.

As with other embodiments, device 90 may be delivered via a catheter and deployed in the coronary sinus to treat mitral valve regurgitation by reshaping the tissue adjacent to focal deflector 98. The device is in a deformed and unexpanded state within the catheter, and self-expands and reforms into the shape shown in FIG. 10 once expelled from the catheter. The anchors 92 and 94 and the anchor portion 100 of focal deflector 98 are further expanded and locked by advancing their respective eyelets over corresponding lock bumps on their proximal sides.

Because of the action of focal deflector 98, the desired reshaping of the mitral valve annulus may be achieved with less or even with no cinching. Thus, the anchors 92 and 94 do not need to anchor as tightly and may be expanded less, thereby minimizing the reshaping of non-target tissue adjacent the anchors. In addition, with less or no cinching, the effect on non-target tissue adjacent the connector is also minimized. Furthermore, because focal deflector 98 is formed similar to an anchor, the presence of focal deflector 98 enables a user to cinch the distal and proximal portions of device 90 with different cinching forces.

Figure 13:
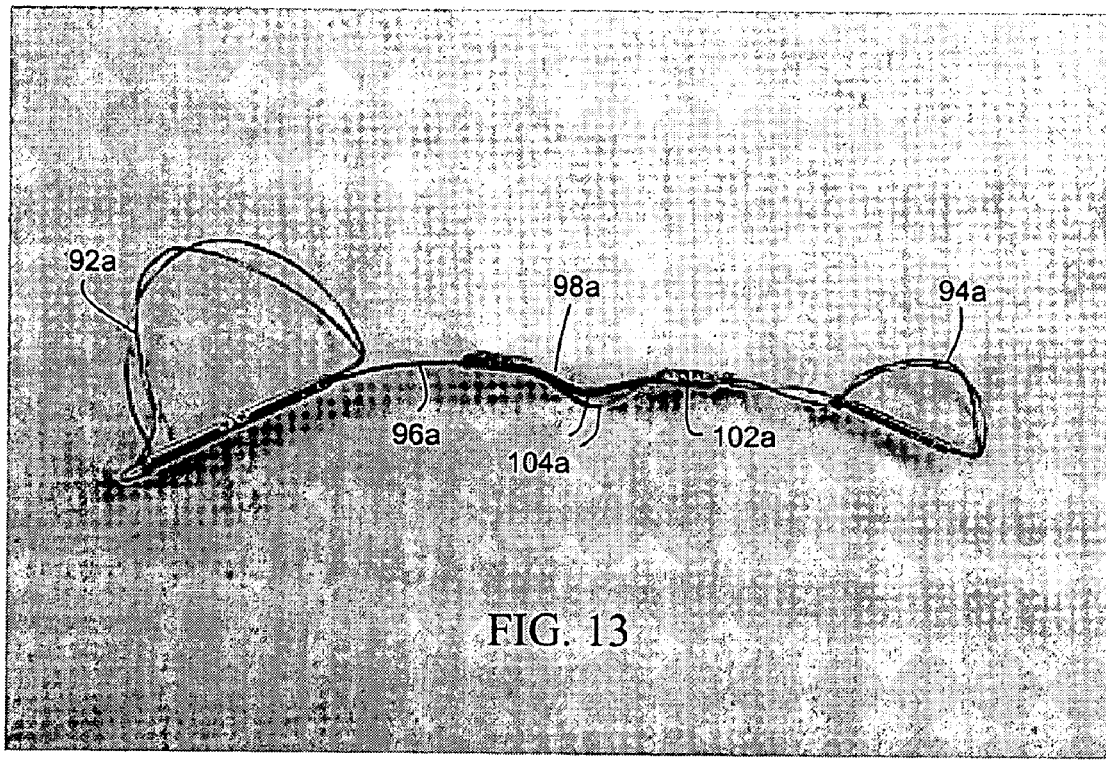
FIG. 13 shows yet another embodiment of the invention.

The embodiment of FIG. 13 omits the wire 100 of focal deflector 98 but is identical to the embodiment of FIGS. 10-12 in all other respects.

Figure 14:
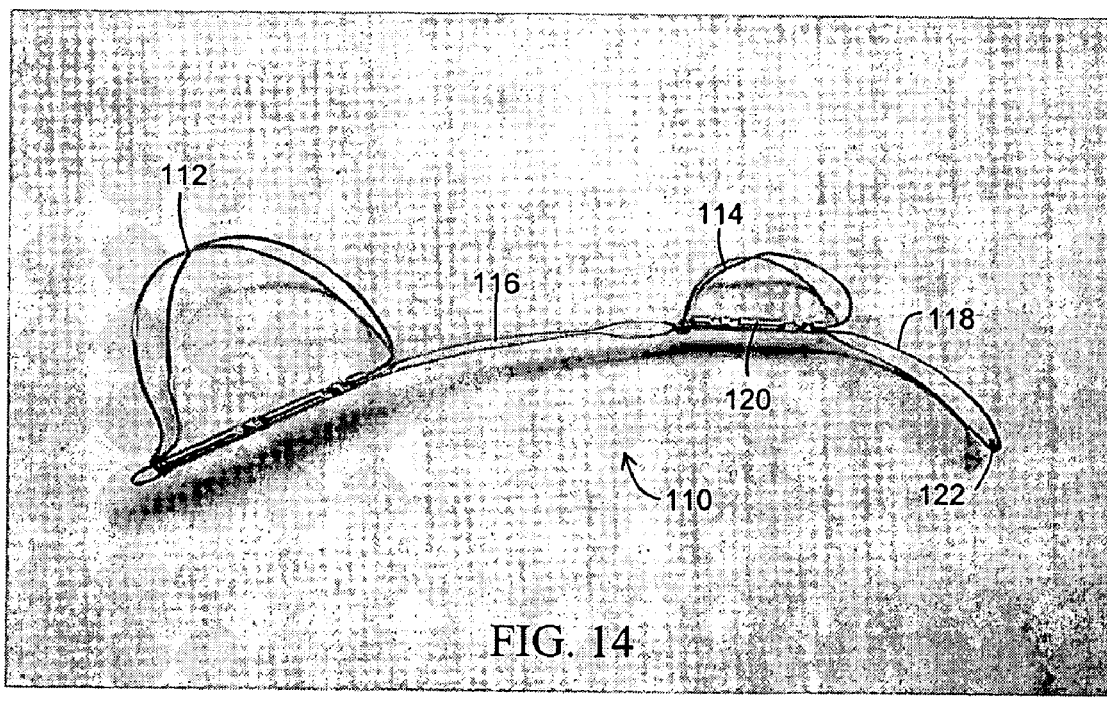
FIG. 14 shows an embodiment of the invention with a tail portion extending from the focal deflector.

FIG. 14 shows an embodiment of a device 110 with a proximal anchor 112 formed in a figure 8 pattern, as in other embodiments. A focal deflector 114 formed as an anchor in a figure 8 pattern, as in the embodiment of FIG. 6, is connected to proximal anchor 112 by a connector 116. A tail 118 extends distally from focal deflector 114 formed from a wire bent in a loop. The loop has a circumference that allows the loop to engage the wall of the vessel in which the device is placed. The points of engagement between the loop and vessel depend on the relative diameters of the loop and vessel. When deployed in a curved vessel, such as the coronary sinus, the loop will follow the vessel's curve to orient the device correctly within the vessel. The ends of the wire are contained with a crimp 120. A small loop 122 is formed at the distal end of tail 118 to provide additional spring action to the tail.

As in the other embodiments, device 110 may be delivered via a catheter and deployed in the coronary sinus to treat mitral valve regurgitation by reshaping the tissue adjacent to focal deflector 114. The device is in a deformed and unexpanded state within the catheter, and self-expands and reforms into the shape shown in FIG. 14 once expelled from the catheter. The proximal anchor 112 and focal deflector 114 are further expanded and locked by advancing their respective eyelets over corresponding lock bumps on their proximal sides.

Element 114 of device 110 in FIG. 14 may be used as a distal anchor instead of as a focal deflector, of course.

Figure 15:
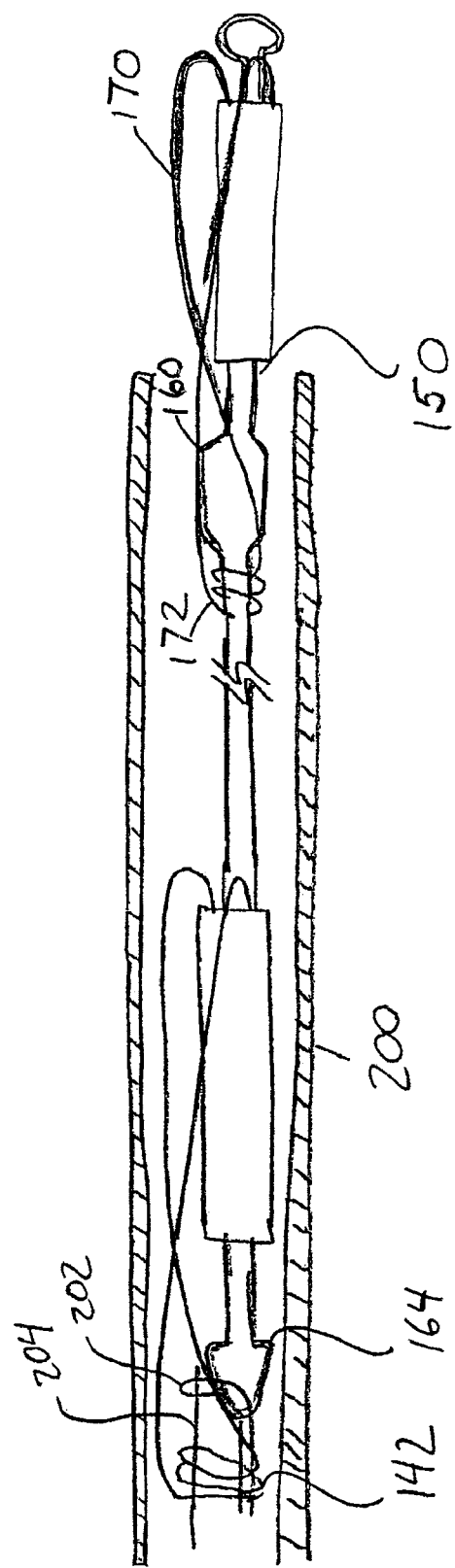
FIG. 15 illustrates one method for delivering an intravascular support to a desired location in the body.

FIG. 15 illustrates one method for delivering an intravascular support 150 in accordance with the present invention to a desired location in the body. As indicated above, intravascular support 150 is preferably loaded into and routed to a desired location within a catheter 200 with the proximal and distal anchors in a collapsed or deformed condition. That is, the eyelet 172 of the distal anchor 170 is positioned proximally of the distal lock 160 and the eyelet 142 of the proximal anchor is positioned proximal to the proximal lock 164. The physician ejects the distal end of the intravascular support from the catheter 200 into the lumen by advancing the intravascular support or retracting the catheter or a combination thereof. A pusher (not shown) provides distal movement of the intravascular support with respect to catheter 200, and a tether provides proximal movement of the intravascular support with respect to catheter 200. Because of the inherent recoverability of the material from which it is formed, the distal anchor begins to expand as soon as it is outside the catheter. Once the intravascular support is properly positioned, the eyelet 172 of the distal anchor is pushed distally over the distal lock 160 so that the distal anchor 170 further expands and locks in place to securely engage the lumen wall and remains in the expanded condition. Next, the proximal end of the support wire is tensioned by applying a proximally-directed force on the support wire and distal anchor to apply sufficient pressure on the tissue adjacent the support wire to modify the shape of that tissue. In the case of the mitral valve, fluoroscopy, ultrasound or other imaging technology may be used to see when the support wire supplies sufficient pressure on the mitral valve to aid in its complete closure with each ventricular contraction without otherwise adversely affecting the patient. Once the proper pressure of the support wire has been determined, the proximal anchor is deployed from the catheter and allowed to begin its expansion. The eyelet 142 of the proximal anchor is advanced distally over the proximal lock 164 to expand and lock the proximal anchor, thereby securely engaging the lumen wall and maintaining the pressure of the support wire against the lumen wall. Finally, the mechanism for securing the proximal end of the intravascular support can be released. In one embodiment, the securement is made with a braided loop 202 at the end of the tether and a hitch pin 204. The hitch pin 204 is withdrawn thereby releasing the loop 202 so it can be pulled through the proximal lock 164 at the proximal end of the intravascular support 150.

Other modifications of the device are within the scope of the invention. For example, the anchors may be of some other design known in the art. In addition, the focal deflector may have some other shape designed to make the desired change in the target tissue.

What is claimed is:

1. A method of modifying target tissue shape comprising:
   providing a tissue shaping device comprising proximal and distal anchors, a connector disposed between the proximal and distal anchors, and a focal deflector;
   placing the tissue shaping device in a lumen adjacent the target tissue;
   expanding the distal anchor to anchor the distal anchor in the lumen;
   applying a proximally directed force on the distal anchor, wherein applying the proximally directed force on the distal anchor applies a shaping force from the focal deflector against the lumen wall to modify the shape of the target tissue; and
   expanding the proximal anchor to anchor the proximal anchor in the lumen,
   wherein anchoring the proximal anchor occurs before ceasing the proximally directed force.

2. The method of claim 1 wherein the lumen has a lumen axis, the placing step comprising orienting the focal deflector away from the lumen axis and toward the target tissue.

3. The method of claim 1 wherein the lumen has a lumen axis, the placing step comprising orienting the focal deflector away from the lumen axis and away from the target tissue.

4. A method of modifying target tissue shape comprising:
   providing a tissue shaping device comprising proximal and distal anchors, a connector disposed between the proximal and distal anchors, and a focal deflector;
   advancing the tissue shaping device to a lumen adjacent the target tissue;
   expanding the distal anchor to anchor the distal anchor in the lumen;
   applying a proximally directed force on the distal anchor, wherein applying the proximally directed force on the distal anchor applies a shaping force from the focal deflector against the lumen wall to modify the shape of the target tissue; and
   expanding the proximal anchor to anchor the proximal anchor,
   wherein expanding the proximal anchor occurs while applying the proximally directed force.

5. A method of modifying target tissue shape comprising:

providing a tissue shaping device comprising an expandable distal anchor, an expandable proximal anchor, a connector disposed between the proximal and distal anchors, and a focal deflector;

advancing the tissue shaping device to a lumen adjacent the target tissue;

anchoring the distal anchor in the lumen;

applying a proximally directed force on the distal anchor, wherein applying the proximally directed force on the distal anchor applies a shaping force from the focal deflector against the lumen wall which modifies the shape of the target tissue, and anchoring the proximal anchor after the shape of the target tissue has been modified.

6. The method of claim 5 wherein anchoring the proximal anchor maintains the modification to the shape of the target tissue caused by the application of the proximally directed force.

* * * * *